US008638443B2

(12) United States Patent
Haran et al.

(10) Patent No.: US 8,638,443 B2
(45) Date of Patent: Jan. 28, 2014

(54) ERROR COMPENSATION IN A SPECTROMETER

(75) Inventors: Frank M. Haran, North Vancouver (CA); Stéphane Savard, Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 262 days.

(21) Appl. No.: 13/114,920

(22) Filed: May 24, 2011

(65) Prior Publication Data

US 2012/0300206 A1 Nov. 29, 2012

(51) Int. Cl.
*G01J 3/45* (2006.01)
(52) U.S. Cl.
USPC ............... 356/452; 356/451; 356/453
(58) Field of Classification Search
USPC .......................................... 356/452
See application file for complete search history.

(56) References Cited

U.S. PATENT DOCUMENTS

| 4,626,773 | A | 12/1986 | Kroeger |
| 4,767,935 | A | 8/1988 | Anderson et al. |
| 4,786,817 | A | 11/1988 | Boissevain et al. |
| 4,830,503 | A | 5/1989 | Hoda et al. |
| 4,920,261 | A | 4/1990 | Bock et al. |
| 4,982,334 | A | 1/1991 | Balakrishnan |
| 5,022,966 | A | 6/1991 | Hu |
| 5,166,758 | A | 11/1992 | Dahlquist |
| 5,396,055 | A | 3/1995 | Shepard et al. |
| 5,539,634 | A | 7/1996 | He |
| 5,773,714 | A | 6/1998 | Shead |
| 5,952,818 | A | 9/1999 | Zhang et al. |
| 6,665,075 | B2 | 12/2003 | Mittleman et al. |
| 6,747,736 | B2 | 6/2004 | Takahashi |
| 7,184,810 | B2 | 2/2007 | Caduff |
| 7,214,940 | B2 | 5/2007 | Cluff et al. |
| 7,242,010 | B2 | 7/2007 | Liu et al. |
| 7,488,940 | B2 | 2/2009 | Ohtake et al. |
| 2002/0074500 | A1 | 6/2002 | Mickan et al. |
| 2004/0065832 | A1 | 4/2004 | Cluff |
| 2006/0109519 | A1 | 5/2006 | Beselt et al. |
| 2006/0243931 | A1 | 11/2006 | Haran et al. |
| 2007/0137823 | A1 | 6/2007 | Haran |
| 2007/0158571 | A1 | 7/2007 | Cole et al. |
| 2008/0079949 | A1* | 4/2008 | Kuroiwa ................. 356/496 |

(Continued)

FOREIGN PATENT DOCUMENTS

| JP | 2002-292832 A | 10/2002 |
| JP | 2007-218662 A | 8/2007 |
| JP | 2008-151591 A | 7/2008 |
| WO | WO 2010/014867 A2 | 2/2010 |

OTHER PUBLICATIONS

Peter H. Siegal, "Terahertz Technology", IEEE Transactions on Microwave Theory and Techniques, vol. 50, No. 3, Mar. 2002, p. 910-928.

L.P. Schmidt, et al., "THz Measurement Technologies and Applications", Microwaves, Radar & Wireless Communications, 2002, Mikon 2002, vol. 2, p. 581-587.

(Continued)

*Primary Examiner* — Tarifur Chowdhury
*Assistant Examiner* — Omar Nixon

(57) ABSTRACT

A method for compensating for errors in a spectrometer is provided that includes measuring at least a portion of a path length for a signal traveling through the spectrometer during a measurement scan of a material. A detector signal corresponding to the measurement scan is generated. Compensation for errors in the detector signal is provided based on the measurement of the path length.

21 Claims, 4 Drawing Sheets

(56) References Cited

U.S. PATENT DOCUMENTS

| | | |
|---|---|---|
| 2008/0165355 A1 | 7/2008 | Yasui |
| 2009/0152469 A1 | 6/2009 | Nishizawa |
| 2010/0007955 A1 | 1/2010 | Beset |
| 2010/0024999 A1 | 2/2010 | Haran |
| 2010/0145650 A1* | 6/2010 | Nahum et al. ............ 702/97 |
| 2010/0282970 A1 | 11/2010 | Haran et al. |

OTHER PUBLICATIONS

U.S. Appl. No. 12/862,733 titled "Continuous Referenceing for Increasing Measurement Precision in Time-Domain Spectroscopy".

Notification of Transmittal of the International Search Report and the Written Opinion of the International Searching Authority, or the Declaration dated Oct. 8, 2012 in connection with International Patent Application No. PCT/US2012/036940.

* cited by examiner

ERROR COMPENSATION IN A SPECTROMETER

TECHNICAL FIELD

This disclosure relates generally to spectroscopy. More specifically, this disclosure relates to error compensation in a spectrometer.

BACKGROUND

Spectroscopy is an important analytical tool for measuring various properties of an object. Recently, terahertz (THz) spectrometry has been developed for analyzing these properties. THz spectroscopy uses visible to near-infrared laser pulses, each lasting only about ten to several hundred femtoseconds, in order to generate electromagnetic pulses (T-rays), which last about a picosecond. These T-rays are then transmitted through an object using an imaging system of lenses and mirrors. Based on the changes in the T-rays as they pass through the object, information may be determined about certain properties of the object. For example, a THz spectrometer may be used in this way to ascertain the caliper, moisture and/or basis weight of paper.

The precision of amplitude and phase measurements in spectroscopy, including THz spectroscopy, is often limited by noise in the system. For example, fluctuations in environmental parameters, such as temperature changes, mechanical vibrations or changes in air composition, may result in pulses that have traveled through the same material reaching the detector at slightly different times and with slightly different amplitudes. Conventional methods of attempting to overcome these errors include attempting to control the environmental parameters. For example, systems may be implemented to minimize changes in temperature and air composition and to minimize vibrations in the system. However, these systems may not be capable of controlling these parameters enough to produce results with a desired degree of accuracy.

SUMMARY

This disclosure describes error compensation in a spectrometer.

In a first embodiment, a method is provided that includes measuring at least a portion of a path length for a signal traveling through a spectrometer during a measurement scan of a material. A detector signal corresponding to the measurement scan is generated. Compensation for errors in the detector signal is provided based on the measurement of the path length.

In a second embodiment, a spectrometer includes an emitter, optical components, a detector and a path length evaluator. The emitter is configured to generate an emitter signal. The optical components are configured to guide the emitter signal through the spectrometer. The detector is configured to generate a detector signal based on the emitter signal. The path length evaluator is configured to measure at least a portion of a path length for the emitter signal.

In a third embodiment, an apparatus includes a Z-distance converter and a detector data corrector. The Z-distance converter is configured to receive a Z-distance measurement corresponding to a measurement scan in a spectrometer. The Z-distance converter is also configured to convert the measured Z-distance into a Z-distance correction. The Z-distance comprises a distance between a first head of the spectrometer and a second head of the spectrometer. The detector data corrector is coupled to the Z-distance converter and is configured to receive the Z-distance correction, to receive a detector signal corresponding to the measurement scan, and to apply the Z-distance correction to the detector signal.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 6, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
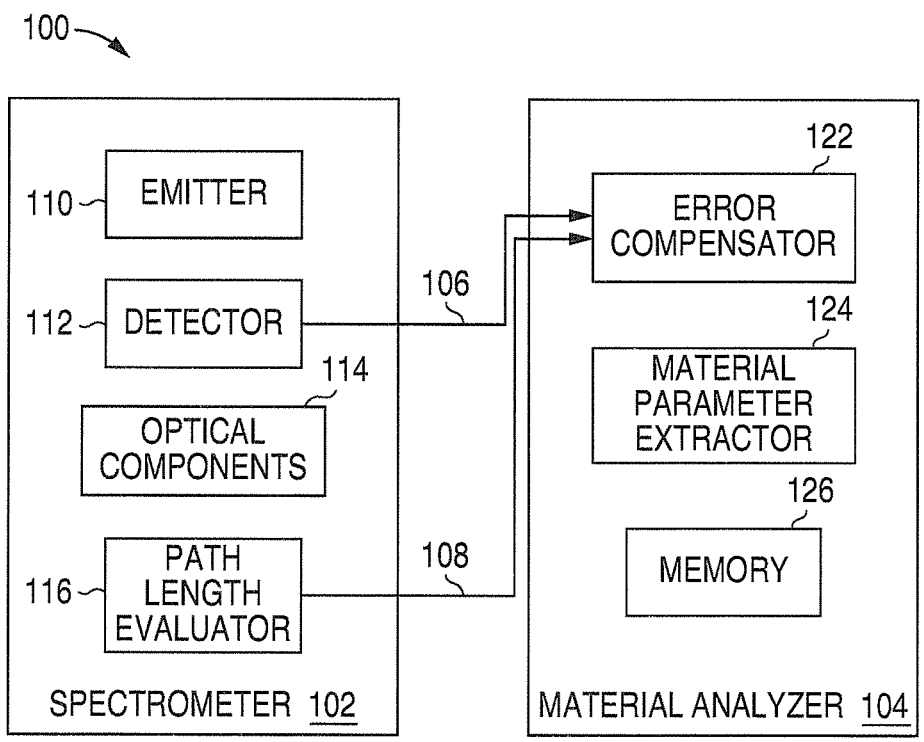
FIG. 1 illustrates a system for compensating for errors in a spectrometer according to one embodiment of this disclosure.

FIG. 1 illustrates a system 100 for compensating for errors in a spectrometer 102 according to one embodiment of this disclosure. For the illustrated embodiment, the system 100 comprises the spectrometer 102 and a material analyzer 104 coupled to the spectrometer 102. For some embodiments, the spectrometer 102 may comprise a THz spectrometer. However, although some of the following description may relate to a THz spectrometer, it will be understood that the spectrometer 102 may comprise any suitable type of spectrometer.

As described in more detail below, the spectrometer 102 is capable of generating an emitter signal, passing the signal through a material to be analyzed, and generating a detector signal 106 based on the signal that has passed through the material. The spectrometer 102 is also capable of measuring at least a portion of the path length of the signal through the spectrometer 102 and of generating a path length signal 108 based on the measurement of the path length. The material analyzer 104 is capable of analyzing the material based on the detector signal 106 and the path length signal 108.

The spectrometer 102 comprises an emitter 110, a detector 112, optical components 114 and a path length evaluator 116. The emitter 110 is capable of receiving an optical signal, such as an optical pulse or a continuous wave, generated by an optical signal source (not shown in FIG. 1), such as a femtosecond pulse laser, near-infrared lasers, a backward-wave oscillator or the like. The optical signal may be modulated or otherwise suitably processed before being provided to the emitter 110. The emitter 110 is capable of generating the emitter signal based on the optical signal. For some embodiments, the emitter 110 may be capable of generating the emitter signal by generating an electrical pulse in the time-domain.

The detector 112 is capable of receiving the optical signal provided to the emitter 110 after the optical signal has been delayed by a specified amount of time. The detector 112 is also capable of receiving a modified signal, which is based on the modification of the emitter signal as it is passed through the material being analyzed, generating the detector signal 106 based on the delayed optical signal and the modified signal, and providing the detector signal 106 to the material analyzer 104.

For some embodiments, both the emitter 110 and the detector 112 may comprise a photoconductive antenna. However, it will be understood that the emitter 110 and/or the detector 112 may comprise any other suitable device, such as Zinc Telluride crystals that may be used for optical rectification.

The optical components 114 are capable of guiding the signal from the emitter 110 through the material and to the detector 112. The optical components 114 may comprise at least one beam splitter, a plurality of mirrors, a plurality of lenses, a plurality of delay stages and/or any other suitable optical devices.

The path length evaluator 116 is capable of measuring at least a portion of the path length of the signal from the emitter 110 through the material and back to the detector 112. The path length evaluator 116 is also capable of generating the path length signal 108 based on this measurement and providing the path length signal 108 to the material analyzer 104.

The material analyzer 104 comprises an error compensator 122, a material parameter extractor 124 and a memory 126. The detector signal 106 may be very sensitive to the path length, especially for the embodiments in which the emitter is capable of generating electrical pulses in the time-domain. Thus, any vibration that alters the path length introduces errors into the detector signal 106. The error compensator 122 is capable of receiving the detector signal 106 and the path length signal 108 and, based on the path length signal 108, compensating the detector signal 106 for errors due to variations in the path length. The error compensator 122 may also be capable of compensating for errors in the detector signal 106 based on additional spectrometer data other than the path length signal 108. Based on the error compensation, the error compensator 122 is capable of generating an error-compensated detector signal.

The material parameter extractor 124 is capable of determining values for the parameters being analyzed in the material based on the error-compensated detector signal generated by the error compensator 122. The memory 126 is capable of storing any suitable data relevant to the analysis of the material. For example, the memory 126 may be capable of storing calibration data suitable for use by the error compensator 122 in correcting errors in the detector signal 106 and/or may be capable of storing calibration data suitable for use by the material parameter extractor 124 in determining the parameter values.

Although FIG. 1 illustrates one example of a system 100 for compensating for errors in a spectrometer 102, various changes may be made to FIG. 1. For example, the arrangement of the system 100 is for illustration only. Thus, various components in FIG. 1 could be combined, further subdivided, or omitted and additional components could be added according to particular needs. For instance, the error compensator 122 and the material parameter extractor 124 are shown as two separate components. However, a single component may be implemented that provides the functionality of both the error compensator 122 and the material parameter extractor 124.

Figure 2:
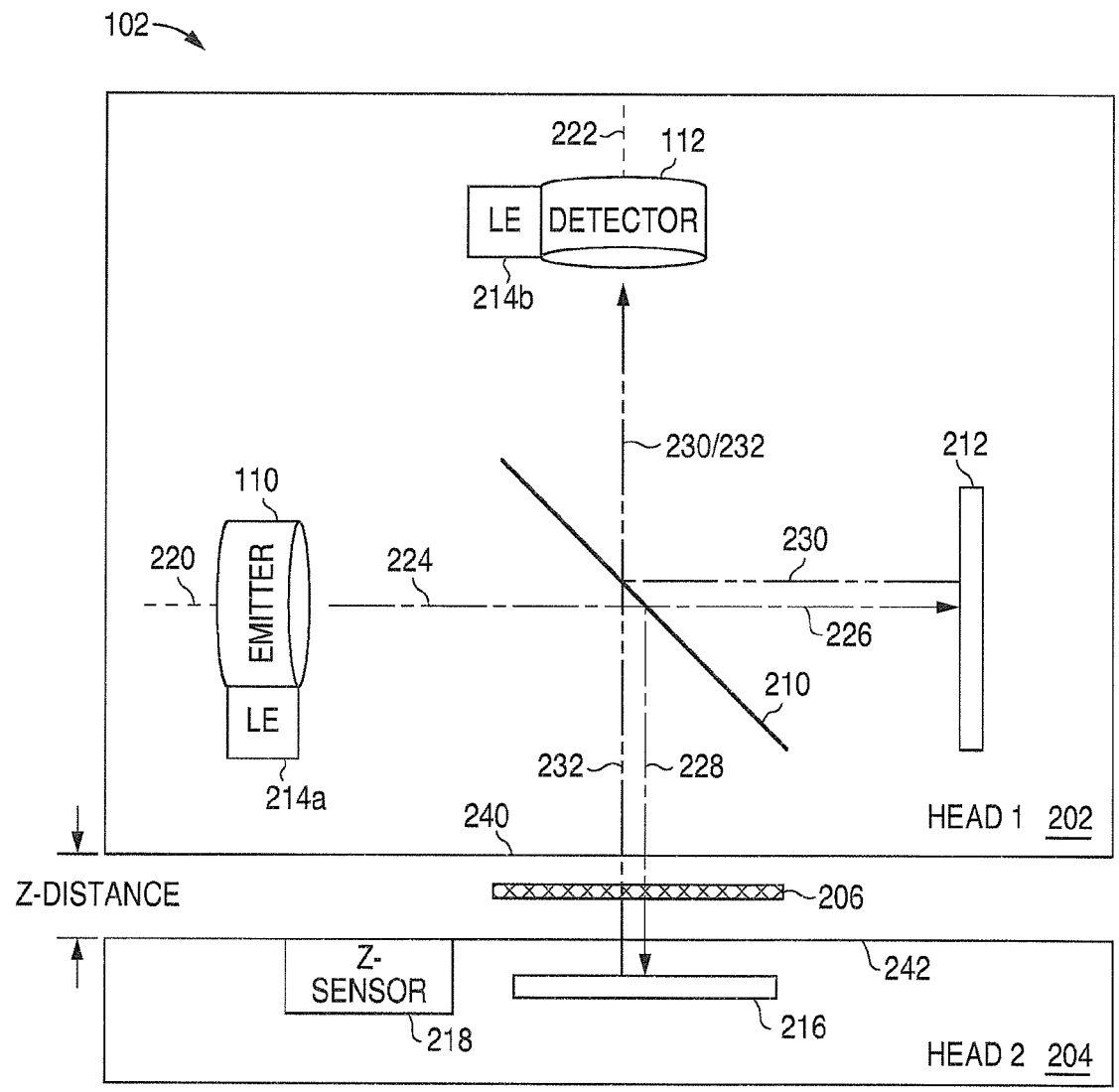
FIG. 2 illustrates details of the spectrometer of FIG. 1 according to one embodiment of this disclosure.

FIG. 2 illustrates details of the spectrometer 102 according to one embodiment of this disclosure. The spectrometer 102 comprises a first head 202 and a second head 204, which are separated by a distance referred to in this disclosure as the Z-distance. The material 206 to be analyzed by the spectrometer 102 passes between the heads 202 and 204 within the space defined by the Z-distance.

For the illustrated embodiment, the optical components 114 comprise a beam splitter 210, a first mirror 212 and a second mirror 216. It will be understood that the optical components 114 may comprise additional components, such as lenses, delay stages, additional mirrors or the like, which are not illustrated in FIG. 2. For some embodiments, the beam splitter 210 may comprise a silicon slab or other suitable material, such as sapphire, polyethylene or the like.

In addition, for the illustrated embodiment, the path length evaluator 116 comprises a first laser encoder (LE) 214a, a second laser encoder 214b and a Z-sensor 218. However, it will be understood that the path length evaluator 116 may comprise any suitable combination of these components 214 and 218. As described in more detail below, each laser encoder 214 is capable of measuring an optic distance, i.e., a distance associated with one of the optical components 114. The Z-sensor 218 is capable of measuring the Z-distance. Because the Z-distance is generally more susceptible to mechanical vibration errors than any of the optic distances, for some embodiments, the spectrometer 102 may be implemented with the Z-sensor 218 but without both or any laser encoders 214.

In operation, an optical signal source (not shown in FIG. 2) generates an optical signal 220 for the emitter 110. A delay element (also not shown in FIG. 2) delays the optical signal 220 to generate a delayed optical signal 222 for the detector 112.

The emitter 110 generates an emitter signal 224 based on the optical signal 220. The emitter signal 224 may be incident on the beam splitter 210 at a 45-degree angle. The beam splitter 210 splits the emitter signal 224 into a transmitted emitter signal 226 provided to the first mirror 212 and a reflected emitter signal 228 provided to the second mirror 216. The first mirror 212 reflects the signal 226 back as a reference signal 230 for the detector 112. The reference signal 230 may be used to track fluctuations in time and amplitude. Because the transmitted and reflected emitter signals 226 and 228 are generated by the emitter 110 at the same time and position, their phases and amplitudes correlate very strongly, and this correlation may be used to correct some measurement errors.

The reflected emitter signal 228 passes through the material 206, where the characteristics of the signal 228 are modified in accordance with the properties of the material 206, before reaching the second mirror 216. The signal 228 is then reflected back through the material 206, where the characteristics are again modified, resulting in a modified signal 232.

The detector 112 receives the reference signal 230 and the modified signal 232. The detector 112 also receives the delayed optical signal 222 at substantially the same time as these signals 230 and 232. Based on the received signals 222, 230 and 232, the detector 112 generates a detector signal 106 for the material analyzer 104.

While the spectrometer 102 is operating in this manner to generate the detector signal 106, the path length evaluator 116 measures at least a portion of the path length of the signals in the spectrometer 102. For example, the Z-sensor 218 is capable of measuring the Z-distance. The first laser encoder 214a may be capable of measuring the distance between the emitter 110 and the beam splitter 210 and/or the distance between the emitter 110 and the first mirror 212. Similarly, the second laser encoder 214b may be capable of measuring the distance between the detector 112 and the beam splitter 210 and/or the distance between the detector 112 and an edge 240 of the first head 202. Thus, when the path length evaluator 116 is capable of measuring each of these distances described above, the entire path length of the signal is measured with the exception of the relatively short distance between an edge 242 of the second head and the second mirror 216. However, if desired, an additional laser encoder 214 may be implemented to measure the distance between the edge 242 and the second mirror 216, thereby allowing the entire path length to be measured. Based on the measurements of the Z-distance and/or the distances between various components of the spectrometer 102, the path length evaluator 116 is capable of generating the path length signal 108, which includes these measurements for use by the error compensator 122.

For some embodiments, each laser encoder 214 may comprise an interferometric encoder capable of measuring distances of less than one nanometer. However, it will be understood that each laser encoder 214 may comprise any suitable device capable of providing relatively precise measurements of the optic distances.

The Z-sensor 218 may comprise an eddy-current sensor that is capable of measuring the Z-distance using induction. This type of sensor is relatively insensitive to low-conducting material sheet parameters. However, it will be understood that the Z-sensor 218 may comprise any suitable component capable of providing relatively precise measurements of the Z-distance. The Z-sensor 218 may be located relatively close to the second mirror 216, and thus the signal path. However, if the Z-sensor 218 is located farther away from the signal path, the Z-distance measurement may be scaled by the error compensator 122 depending on the design of the heads 202 and 204 and the frame holding the heads 202 and 204.

Although FIG. 2 illustrates one example of the spectrometer 102, various changes may be made to FIG. 2. For example, the arrangement of the spectrometer 102 is for illustration only. Thus, various components in FIG. 2 could be combined, further subdivided, or omitted and additional components could be added according to particular needs. For instance, although illustrated as part of the second head 204, the Z-sensor 218 may instead be implemented in the first head 202.

Figure 3:
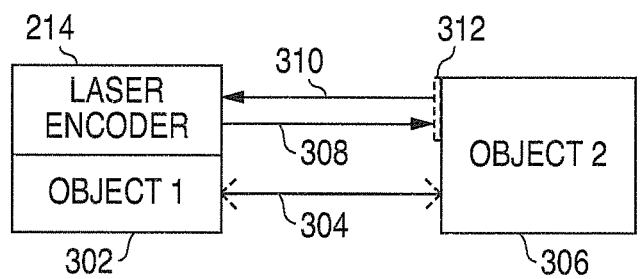
FIG. 3 illustrates the operation of one of the laser encoders of FIG. 2 according to one embodiment of this disclosure.

FIG. 3 illustrates the operation of one of the laser encoders 214 according to one embodiment of this disclosure. For this embodiment, the laser encoder 214 may be coupled to, or located relatively close to, a first object 302 in the first head 202 of the spectrometer 102. The first object 302 may be capable of sending a signal 304 to, or receiving a signal 304 from, a second object 306 in the first head 202 of the spectrometer 102. The first object 302 may correspond to the emitter 110 or the detector 112 and the second object 306 may correspond to the beam splitter 210, the first mirror 212, the edge 240 of the first head 202 and/or any other suitable optical component of the first head 202.

At substantially the same time as the signal 304 is being sent between the objects 302 and 306, the laser encoder 214 is capable of directing a laser signal 308 to the second object 306, which reflects back to the laser encoder 214 a reflected laser signal 310. Based on the reflected laser signal 310, the laser encoder 214 is capable of determining an optic distance, i.e., the distance between the objects 302 and 306. The laser encoder 214 is also capable of providing this distance to the material analyzer 104 as part of the path length signal 108.

For some embodiments, an optional reflector 312 may be coupled to the second object 306. The reflector 312 may comprise a mirror, retroreflector or other suitable reflective material capable of reflecting the laser signal 308 back to the laser encoder 214.

Figure 4:
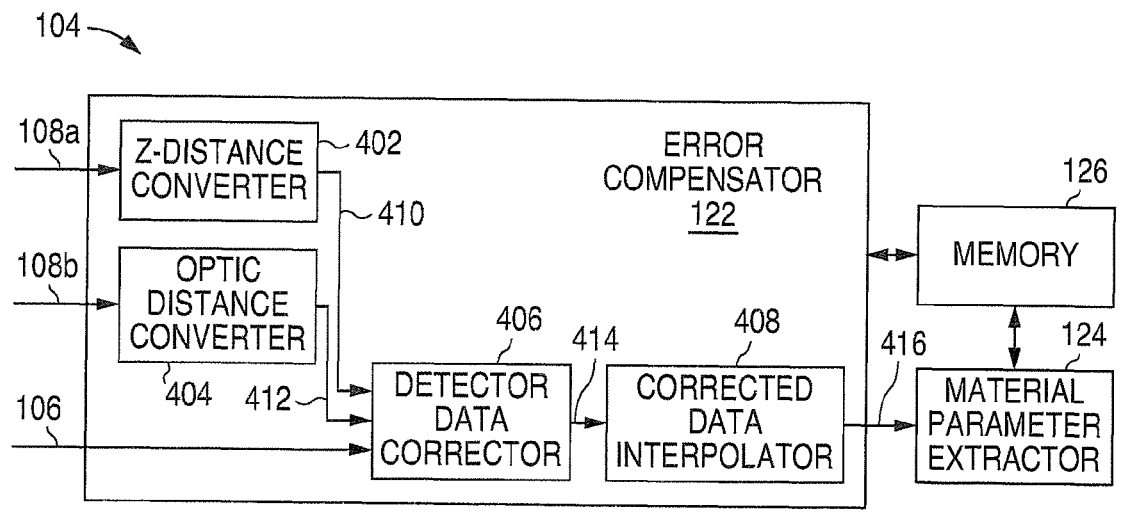
FIG. 4 illustrates details of the material analyzer of FIG. 1 according to one embodiment of this disclosure.

FIG. 4 illustrates details of the material analyzer 104 according to one embodiment of this disclosure. For the illustrated embodiment, the error compensator 122 comprises a Z-distance converter 402, an optic distance converter 404, a detector data corrector 406 and a corrected data interpolator 408.

The Z-distance converter 402 is capable of receiving a portion of the path length signal 108a corresponding to the Z-distance measurement determined by the Z-sensor 218. The Z-distance converter 402 is also capable of converting the measured Z-distance into a Z-distance correction 410 for the detector signal 106.

The optic distance converter 404 is capable of receiving a portion of the path length signal 108b corresponding to the optic distance measurements determined by the laser encoders 214. The optic distance converter 404 is also capable of converting the measured optic distances into an optic distance correction 412 for the detector signal 106.

The detector data corrector 406 is coupled to the Z-distance converter 402 and the optic distance converter 404 and is capable of receiving the detector signal 106, in addition to the corrections 410 and 412 corresponding to variations in the path length. The detector data corrector 406 is also capable of correcting the detector signal 106 in accordance with the received corrections 410 and 412 in order to generate corrected detector data 414.

The corrected data interpolator 408 is coupled to the detector data corrector 406 and is capable of receiving the corrected detector data 414 and interpolating the data 414 to obtain equidistant delays for the application of numerical FFT. The corrected data interpolator 408 is also capable of generating an error-compensated detector signal 416 from the interpolated data and providing the error-compensated detector signal 416 to the material parameter extractor 124.

The material parameter extractor 124 is coupled to the error compensator 122 and is capable of receiving the error-compensated detector signal 416 and determining values for the desired parameters of the material 206 based on the error-compensated detector signal 416. The material parameter extractor 124 may use the corrected data corresponding to the reference signal 230 and the modified signal 232, along with calibration data, to determine the parameter values. For one particular embodiment, the material parameter extractor 124 is capable of determining the parameter values by Fourier transforming time-domain data in the error-compensated detector signal 416 to obtain frequency characteristics corresponding to the parameters.

The memory 126 is coupled to the error compensator 122 and the material parameter extractor 124 and is capable of storing calibration data and other data useful to the error compensator 122 and the material parameter extractor 124. For example, the memory 126 may be capable of storing an estimate of the refractive index and density for a dry sample of the material 206.

Although FIG. 4 illustrates one example of the material analyzer 104, various changes may be made to FIG. 4. For example, the arrangement of the material analyzer 104 is for illustration only. Thus, various components in FIG. 4 could be combined, further subdivided, or omitted and additional components could be added according to particular needs. For instance, the Z-distance converter 402 and the optic distance converter 404 are shown as two separate components. However, a single distance converter may be implemented that provides the functionality of both these converters 402 and 404. In addition, for an embodiment in which the spectrometer 102 comprises no laser encoders 214, the optic distance converter 404 may be omitted. As another example, although shown as separate signals, the path length signals 108a and 108b may be provided to the error compensator 122 as a single path length signal 108, and the distance converters 402 and 404 may each be capable of retrieving the appropriate data from the signal 108 to perform its conversion. Alternatively, an additional component may be included that is capable of separating the Z-distance data from the optic distance data for the converters 402 and 404.

Figure 5:
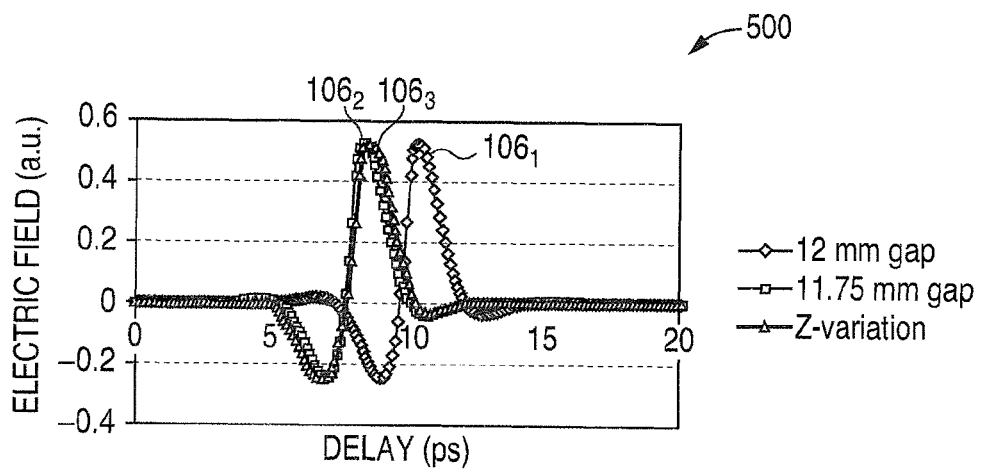
FIG. 5 is a graph illustrating the effect of errors on a typical temporal pulse output from the spectrometer of FIG. 1 according to one embodiment of this disclosure.

FIG. 5 is a graph 500 illustrating the effect of errors due to Z-distance variations on a typical temporal pulse output from the spectrometer 102 according to one embodiment of this disclosure. The graph 500 illustrates the pulse output as an electric field variation in the detector signal 106 with respect to a delay.

In FIG. 5, the graph 500 shows one example of an accurate detector signal $106_1$, which corresponds to an expected Z-distance (based on a calibration measurement) of mm. However, if an outside force such as random vibration changes the Z-distance to 11.75 mm for the duration of the measurement window, i.e., the time for a signal to travel through the spectrometer 102 and provide a single measurement scan, an inaccurate detector signal $106_2$ would result. Furthermore, if the Z-distance is close to 11.75 but varies during the measurement window, additional distortion is introduced such that a distorted inaccurate detector signal $106_3$ would result.

The delay associated with the detector signal 106 is used by the material parameter extractor 124 to determine the parameter values for the material 206. For example, when the delay is larger, the material parameter extractor 124 may determine that the material 206 is thicker. Thus, in order for the material parameter extractor 124 to obtain accurate values for the parameters of the material 206, the detector data corrector 406 corrects errors in the delay in the detector signal 106.

Although FIG. 5 illustrates one example of the errors introduced by Z-distance variations, it will be understood that similar errors may be introduced by optic distance variations. However, the Z-distance is generally more susceptible to mechanical vibration errors than any of the optic distances. For a particular embodiment, the Z-distance may comprise about one centimeter, while vibrations may be on the order of tens of microns, which translates to relatively large errors. Variations in optic distances, however, may comprise a much smaller percentage of the optic distances and, thus, result in smaller errors.

In order to generate an accurate Z-distance correction 410 (which corresponds to the accurate detector signal $106_1$) for Z-distance variations, the Z-distance converter 402 is capable of generating at least two corrections for the delay based on the path length signal 108a. For example, if the path length signal 108a corresponds to the distorted inaccurate detector signal $106_3$, the Z-distance converter 402 may generate a first correction based on the change in the Z-distance during the measurement window (which would result in the inaccurate detector signal $106_2$), followed by a second correction based on the mean change in the Z-distance as compared to the expected Z-distance (which would result in the accurate detector signal $106_1$). The Z-distance converter 402 may then provide the combination of those corrections as the Z-distance correction 410 to the detector data corrector 406, which may apply that Z-distance correction 410 to the distorted inaccurate detector signal $106_3$ received from the detector 112 in order to obtain the accurate detector signal $106_1$.

Similarly, if the Z-distance remains constant during the measurement window, the path length signal 108a corresponds to the inaccurate detector signal $106_2$. In this case, the Z-distance converter 402 may generate a single correction based on the mean change in the Z-distance as compared to the expected Z-distance (which would result in the accurate detector signal $106_1$). The Z-distance converter 402 may then provide that correction as the Z-distance correction 410 to the detector data corrector 406, which may apply that Z-distance correction 410 to the inaccurate detector signal $106_2$ received from the detector 112 in order to obtain the accurate detector signal $106_1$.

Finally, if the path length signal 108a corresponds to the accurate detector signal $106_1$, the Z-distance converter 402 may generate a Z-distance correction 410 that results in the detector data corrector 406 applying no correction to the accurate detector signal $106_1$ received from the detector 112 (with regard to Z-distance changes).

The optic distance converter 404 is capable of generating the optic distance correction 412 in a similar manner to the Z-distance converter 402 generating the Z-distance correction 410. Thus, based on the measurements provided by the laser encoders 214 in the path length signal 108b, the optic distance converter 404 is capable of generating corrections for the detector signal 106 when those measurements vary from expected distances between the components of the spectrometer 102.

The optic distance converter 404 may then provide the combination of those corrections (or a single correction or no correction) as the optic distance correction 412 to the detector data corrector 406, which may apply that optic distance correction 412 to the detector signal 106 received from the detector 112 in order to correct for any changes in distances between the components corresponding to a particular measurement scan.

Therefore, in order to generate corrected detector data 414, the detector data corrector 406 is capable of applying the corrections 410 and 412 to the detector signal 106 received from the detector 112. It will be understood that the detector data corrector 406 may also be capable of applying any other suitable corrections.

In operation, according to a particular embodiment, at least one calibration scan is performed without any material 206 between the heads 202 and 204. From the calibration scan, expected values for the Z-distance and/or optic distances may be determined. The material analyzer 104 may store this calibration data in the memory 126. After the calibration data is determined, material 206 may be passed between the heads 202 and 204 for analysis and measurement scans may be performed.

Assume that the calibration scan is S1. For a given measurement M in S1, the total delay at M (i.e., $Td_{MS1}$) may be described as the sum of a constant K and two times the Z-distance (i.e., $Z_{MS1}$) divided by the speed of light c, as follows:

$$Td_{MS1} = K + \frac{2Z_{MS1}}{c} \qquad \text{Eq. 1}$$

During a second scan S2 or subsequent scans, which may be measurement scans, the constant K at M is assumed the same but the Z-distance is not. Thus, the total delay for S2 is as follows:

$$Td_{MS2} = K + \frac{2Z_{MS2}}{c} \qquad \text{Eq. 2}$$

In the constant-Z scenario, the correction at the measurement M for S2 ($Td_{CorrMS2}$) is given by the difference of the total delay between the calibration scan MS1 and the measurement scan MS2, as follows:

$$Td_{CorrMS2} = Td_{MS1} - Td_{MS2} \qquad \text{Eq. 3}$$

For the scenario where the Z-distance is not a constant over the scanning time but instead depends on the measurement time (i.e., $t_M$), the equations 1 and 2 may now be rewritten as a function of $t_M$, as follows:

$$Td_{MS1}(t_M) = K + \frac{2Z_{MS1}(t_M)}{c} \qquad \text{Eq. 4}$$

$$Td_{MS2}(t_M) = K + \frac{2Z_{MS2}(t_M)}{c} \qquad \text{Eq. 5}$$

Each scan (including the calibration scan) may be corrected by subtracting the delay associated with the Z-distance variation (i.e., $2\Delta Z/c$) around the mean value for the Z-distance, as follows:

$$Td_{corrMS} - Td_{MS} - \frac{2\Delta Z_{MS}(t_M)}{c} \qquad \text{Eq. 6}$$

where $\Delta Z$ is defined as follows:

$$\Delta Z_{MS}(t_M) = Z_{MS}(t_M) - \text{mean}[Z_{MS}(t_M)] \qquad \text{Eq. 7}$$

At this point, the correction in equation 3 may be applied as if the data were in the constant-Z scenario.

Figure 6:
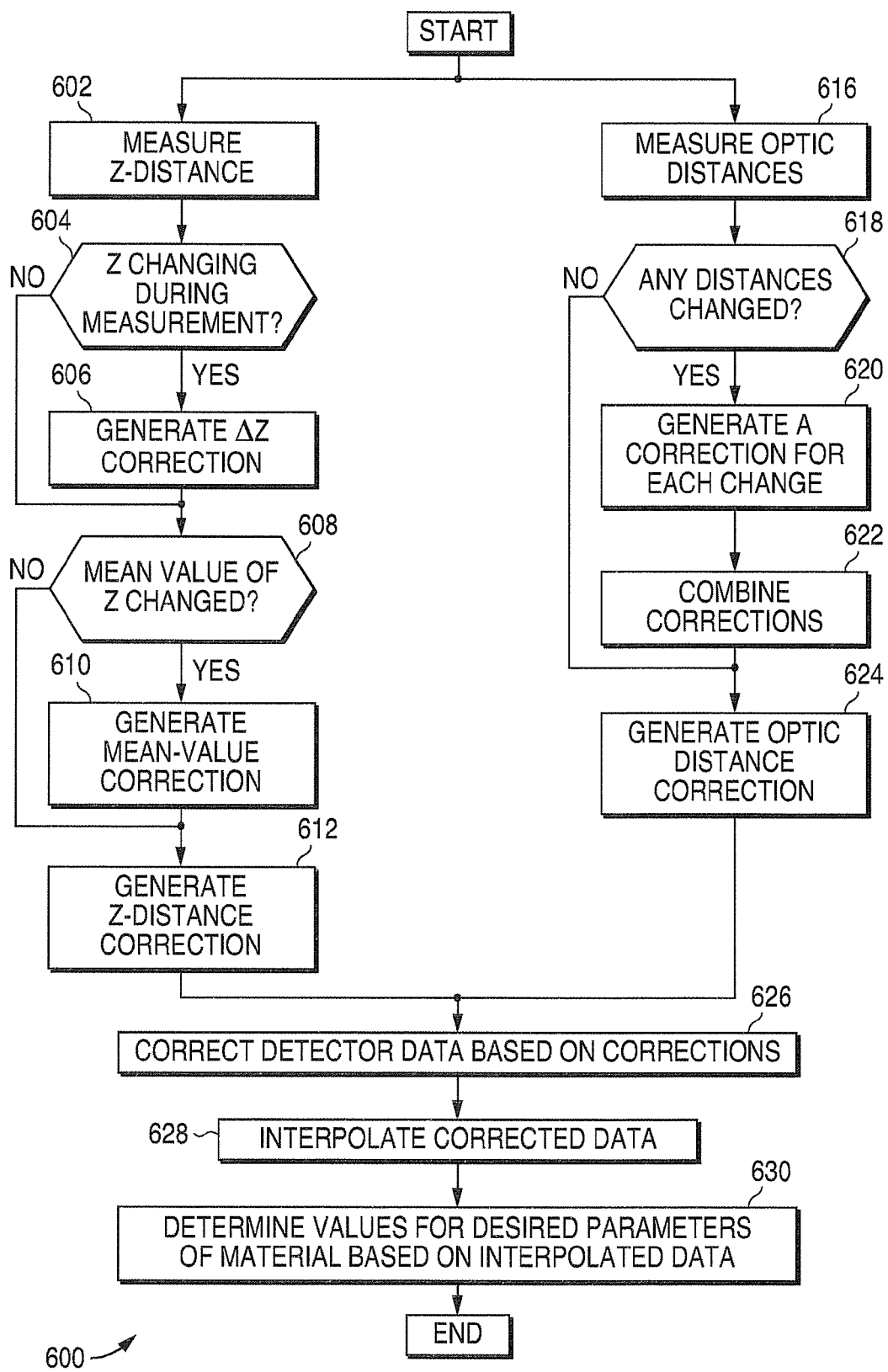
FIG. 6 illustrates a method for compensating for errors in the spectrometer of FIG. 1 according to one embodiment of this disclosure.

FIG. 6 illustrates a method 600 for compensating for errors in a spectrometer 102 according to one embodiment of this disclosure. The embodiment of the method 600 is for illustration only. Other embodiments of the method 600 may be implemented without departing from the scope of this disclosure. The method 600 corresponds to a particular measurement window, i.e., the method 600 may be performed to compensate for the errors in a single measurement scan. It will be understood that the method 600 may be repeated for any number of measurement windows.

As shown in FIG. 6, the method 600 includes measuring the Z-distance between the heads 202 and 204 at step 602. For example, the Z-sensor 218 may measure the Z-distance with induction using eddy currents or in any other suitable manner. A determination is made regarding whether or not the value of the Z-distance was changing during the measurement window at step 604. For example, the Z-distance converter 402 may calculate the Z-distance variation for the measurement window and determine that the Z-distance was changing if the variation is non-zero and that the Z-distance was not changing if the variation is zero.

If the Z-distance has changed during the measurement window, a $\Delta Z$ correction is generated at step 606. For example, the Z-distance converter 402 may generate the $\Delta Z$ correction by converting the change in the Z-distance into a corresponding $\Delta Z$ delay. Thus, for a particular example, the $\Delta Z$ delay may correspond to the difference between the distorted inaccurate detector signal $106_3$ and the inaccurate detector signal $106_2$.

A determination is made regarding whether or not the mean value of the Z-distance for the measurement window has changed from an expected mean value at step 608. For example, the Z-distance converter 402 may compare the current measurement of the mean value of the Z-distance, which is provided through the path length signal 108a, to the expected mean value, which may be stored in the memory 126 or other suitable component, in order to determine whether the current mean value is different from the expected mean value.

If the mean value of the Z-distance has changed, a mean-value correction is generated at step 610. For example, the Z-distance converter 402 may generate the mean-value correction by converting the change in the mean value of the Z-distance into a corresponding mean-value delay. Thus, for a particular example, the mean-value delay may correspond to the difference between the inaccurate detector signal $106_2$ and the accurate detector signal $106_1$.

A Z-distance correction 410 is generated based on any $\Delta Z$ correction and/or mean-value correction at step 612. Thus, for example, the Z-distance converter 402 may generate the Z-distance correction 410 by providing the $\Delta Z$ correction, if any, and the mean-value correction, if any, to the detector data corrector 406 as the Z-distance correction 410.

The optic distances may also be measured at step 616. For example, the laser encoders 214 may measure one or more optic distances. It will be understood that, if the optic distances are measured, these measurements are performed at substantially the same time as the measurement of the Z-distance in step 602. A determination is made regarding whether or not the value of any of the measured optic distances changed during the measurement window at step 618. For example, the optic distance converter 404 may determine whether any of the measured optic distances was changing during the measurement window and/or whether the mean value of any of those distances has changed from an expected value.

If any of the optic distances has changed during the measurement window or any of the mean values of the optic distances is different from expected values, a correction is generated for each such change at step 620. For example, the optic distance converter 404 may generate a correction by converting the change in a mean value for a particular optic distance into a corresponding optic delay.

If corrections are generated for more than one optic distance, the corrections are combined at step 622. For example, the optic distance converter 404 may combine the corrections by adding together the optic delays. An optic distance correction 412 is generated at step 624. Thus, for example, the optic distance converter 404 may generate the optic distance correction 412 by providing the correction, if any, or the combined corrections, if any, to the detector data corrector 406 as the optic distance correction 412.

Detector data is corrected based on any corrections at step 626. For example, the detector data corrector 406 may apply the Z-distance correction 410, if any, to the detector signal 106 to correct for any changes in the Z-distance and may apply the optic distance correction 412, if any, to the detector signal 106 to correct for any changes in the optic distances. The corrected detector data 414 is interpolated at step 628. For example, the corrected data interpolator 408 may interpolate the corrected detector data 414 to obtain equidistant delays and generate an error-compensated detector signal 416.

Values for the desired parameters of the material 206 are determined based on the error-compensated detector signal 416 at step 630. For example, the material parameter extractor 124 may determine the values of the parameters based on comparisons of the error-compensated detector signal 416 to parameter data stored in the memory 126. In this way, the accuracy of the parameter values determined by the material parameter extractor 124 may be greatly improved.

Although FIG. 6 illustrates an example of a method 600 for compensating for errors in a spectrometer 102, various changes may be made to this method 600. For example, it will be understood that the determinations made in steps 604, 608 and/or 618 may be omitted and instead the error compensator 122 may perform the correction calculations based on the assumption that variations and changes have occurred. If any of the variations or changes is zero, however, the calculations will provide the appropriate solutions, resulting in no correction for that variation or change of zero. Also, the steps in the method 600 may overlap, occur in parallel, occur multiple times, or occur in a different order.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The term "each" means every one of at least a subset of the identified items. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
obtaining a measurement of at least a portion of a path length for a signal traveling through a spectrometer during a measurement scan of a material;
obtaining a detector signal corresponding to the measurement scan; and
compensating for one or more errors in the detector signal based on the measurement, wherein the compensating comprises correcting the detector signal based on the measurement;
wherein obtaining the measurement comprises obtaining a measurement of at least one optic distance in one or more heads of the spectrometer; and wherein compensating for the one or more errors in the detector signal comprises:
determining a change in the at least one optic distance; and
correcting the detector signal based on the change in the at least one optic distance.

2. The method of claim 1, wherein obtaining the measurement comprises obtaining a measurement of a Z-distance between a first head of the spectrometer and a second head of the spectrometer.

3. The method of claim 2, wherein compensating for the one or more errors in the detector signal comprises:
determining a variation in the Z-distance during the measurement scan;
determining a change in a mean value of the Z-distance for the measurement scan; and
correcting the detector signal based on the variation in the Z-distance and based on the change in the mean value of the Z-distance.

4. The method of claim 2, wherein correcting the detector signal further comprises:
correcting the detector signal based on a difference between an expected delay in the detector signal and an actual delay in the detector signal, the difference due to a variation in the Z-distance and a change in a mean value of the Z-distance.

5. A method comprising:
obtaining a measurement of at least a portion of a path length for a signal traveling through a spectrometer during a measurement scan of a material;
obtaining a detector signal corresponding to the measurement scan; and
compensating for one or more errors in the detector signal based on the measurement, wherein the compensating comprises correcting the detector signal based on the measurement;
wherein obtaining the measurement comprises obtaining measurements of optic distances in one or more heads of the spectrometer, the measurements including:
a measurement of a first optic distance between an emitter and a beam splitter;
a measurement of a second optic distance between the emitter and a mirror;
a measurement of a third optic distance between a detector and the beam splitter; and
a measurement of a fourth optic distance between the detector and an edge of a first of the one or more heads.

6. The method of claim 5, wherein correcting the detector signal comprises:
determining a change in the optic distances; and
correcting the detector signal based on the change in the optic distances.

7. The method of claim 5, wherein correcting the detector signal further comprises:
correcting the detector signal based on a difference between an expected delay in the detector signal and an actual delay in the detector signal, the difference due to a variation in a Z-distance during the measurement scan and a change in a mean value of the Z-distance for the measurement scan.

8. A system comprising:
a spectrometer comprising:
an emitter configured to generate an emitter signal;
a plurality of optical components configured to guide the emitter signal through the spectrometer;

a detector configured to generate a detector signal based on the emitter signal; and a path length evaluator configured to generate a measurement of at least a portion of a path length for the emitter signal; and an analyzer configured to correct the detector signal based on the measurement;

wherein the path length evaluator comprises at least one laser encoder configured to measure at least one optic distance between a first object and a second object in a first head of the spectrometer.

9. The system of claim 8, wherein the path length evaluator further comprises a Z-sensor configured to measure a Z-distance between the first head of the spectrometer and a second head of the spectrometer.

10. The system of claim 9, wherein the Z-sensor comprises an eddy-current sensor.

11. The system of claim 8, wherein the path length evaluator is configured to generate:

a measurement of a first optic distance between an emitter and a beam splitter;

a measurement of a second optic distance between the emitter and a mirror;

a measurement of a third optic distance between a detector and the beam splitter; and a measurement of a fourth optic distance between the detector and an edge of the head.

12. The system of claim 9, wherein the analyzer is configured to correct the detector signal by determining a difference between an expected delay in the detector signal and an actual delay in the detector signal, the difference due to a variation in the Z-distance and a change in a mean value of the Z-distance.

13. A spectrometer comprising:

an emitter configured to generate an emitter signal;

a plurality of optical components configured to guide the emitter signal through the spectrometer;

a detector configured to generate a detector signal based on the emitter signal; and a path length evaluator configured to measure at least a portion of a path length for the emitter signal;

wherein the path length evaluator comprises at least one laser encoder configured to measure at least one optic distance between a first object and a second object in a head of the spectrometer.

14. The spectrometer of claim 13, wherein the at least one laser encoder comprises at least one interferometric encoder.

15. The spectrometer of claim 13, further comprising a reflector coupled to the second object;

wherein the at least one laser encoder is configured to measure the at least one optic distance by directing a laser signal to the second object; and wherein the reflector is configured to reflect the laser signal back to the at least one laser encoder.

16. The spectrometer of claim 13, wherein the at least one laser encoder comprises:

a first laser encoder configured to measure a first optic distance between the emitter and a first one of the optical components; and a second laser encoder configured to measure a second optic distance between the detector and a second one of the optical components.

17. The spectrometer of claim 15, wherein the reflector comprises one of: a mirror or a retroreflector.

18. The spectrometer of claim 16, wherein:

the first laser encoder is coupled to the emitter; and the second laser encoder is coupled to the detector.

19. An apparatus comprising:

at least one distance converter configured to receive a measured distance corresponding to a measurement scan in a spectrometer and to convert the measured distance into a distance correction, wherein the measured distance comprises a measurement of at least a portion of a path length for a signal used by the spectrometer during the measurement scan; and a detector data corrector configured to receive the distance correction, to receive a detector signal corresponding to the measurement scan, and to apply the distance correction to the detector signal;

wherein the at least one distance converter comprises a Z-distance converter configured to determine a variation in a Z-distance during the measurement scan and to determine a change in a mean value of the Z-distance for the measurement scan;

wherein the Z-distance converter is configured to convert the measured distance into the distance correction by determining a difference between an expected delay in the detector signal and an actual delay in the detector signal due to the variation in the Z-distance and the change in the mean value of the Z-distance; and wherein the distance correction comprises the difference between the expected delay and the actual delay.

20. The apparatus of claim 19, wherein:

the at least one distance converter further comprises an optic distance converter configured to receive at least one optic distance measurement corresponding to the measurement scan and to convert the measured optic distance into an optic distance correction; and the detector data corrector is configured to receive the optic distance correction and to apply the optic distance correction to the detector signal.

21. The apparatus of claim 20, wherein a head of the spectrometer comprises an emitter, a detector, a beam splitter and a mirror, and wherein the at least one optic distance measurement comprises:

a first optic distance measurement corresponding to a distance between the emitter and the beam splitter;

a second optic distance measurement corresponding to a distance between the emitter and the mirror;

a third optic distance measurement corresponding to a distance between the detector and the beam splitter; and a fourth optic distance measurement corresponding to a distance between the detector and an edge of the first head.

* * * * *